United States Patent
Chiu et al.

(10) Patent No.: US 10,407,720 B2
(45) Date of Patent: Sep. 10, 2019

(54) METHODS FOR FULL-LENGTH AMPLIFICATION OF DOUBLE-STRANDED LINEAR NUCLEIC ACIDS OF UNKNOWN SEQUENCES

(71) Applicant: ACADEMIA SINICA, Taipei (TW)

(72) Inventors: Kuo Ping Chiu, Changhwa County (TW); Yu-Shin Nai, New Taipei (TW)

(73) Assignee: Academia Sinica, Taipei (TW)

( * ) Notice: Subject to any disclaimer, the term of this patent is extended or adjusted under 35 U.S.C. 154(b) by 385 days.

(21) Appl. No.: 15/037,322

(22) PCT Filed: Dec. 14, 2014

(86) PCT No.: PCT/US2014/070226
§ 371 (c)(1),
(2) Date: May 17, 2016

(87) PCT Pub. No.: WO2015/089496
PCT Pub. Date: Jun. 18, 2015

(65) Prior Publication Data
US 2016/0298172 A1    Oct. 13, 2016

Related U.S. Application Data

(60) Provisional application No. 61/916,271, filed on Dec. 15, 2013.

(51) Int. Cl.
*C12Q 1/686* (2018.01)
*G16B 30/00* (2019.01)
(Continued)

(52) U.S. Cl.
CPC .......... *C12Q 1/686* (2013.01); *C12Q 1/6855* (2013.01); *C12Q 1/6869* (2013.01);
(Continued)

(58) Field of Classification Search
None
See application file for complete search history.

(56) References Cited

U.S. PATENT DOCUMENTS

2003/0096235 A1*  5/2003  Dong ............... C12N 15/1093
                                                        435/6.16
2012/0157322 A1*  6/2012  Myllykangas ....... C12Q 1/6837
                                                        506/2
2012/0208706 A1   8/2012  Downing et al.

OTHER PUBLICATIONS

Tucker et al. The American Journal of Human Genetics 2009; 85: 142-154. (Year: 2009).*

(Continued)

*Primary Examiner* — Angela M. Bertagna
(74) *Attorney, Agent, or Firm* — Hsiu-Ming Saunders; Intellectual Property Connections, Inc.

(57) ABSTRACT

An adaptor for use in amplifying all linear, double-stranded nucleic acid molecules of unknown sequences in a sample is disclosed. The adaptor consists of: (1) the first oligonucleotide (P-oligo) with a phosphate at the 5' end and without an additional thymine nucleotide at the 3' end; and (2) the second oligonucleotide (T~oligo) with an extra 3'-T and without a 5'-phosphate. The P-oligo and T-oligo are complementary to each other except at the 3'-T (thymine) in the T-oligo. The adaptor is ligated to nucleic acids of unknown sequences which have an extra A in the 3' end (3'~A overhang) to form adaptor-ligated target nucleic acids. The T-oligo is then employed as a single primer for T-oligo-primed polymerase chain reaction (TOP-PCR) and amplifies the nucleic acids of unknown sequences in full-length.

16 Claims, 5 Drawing Sheets

Specification includes a Sequence Listing.

(51) Int. Cl.
  *C12Q 1/6869* (2018.01)
  *C12Q 1/6886* (2018.01)
  *C12Q 1/6855* (2018.01)
  *G16B 35/00* (2019.01)
  *G16C 20/60* (2019.01)

(52) U.S. Cl.
  CPC ........... *C12Q 1/6886* (2013.01); *G16B 30/00* (2019.02); *G16B 35/00* (2019.02); *G16C 20/60* (2019.02); *C12Q 2600/156* (2013.01)

(56) References Cited

OTHER PUBLICATIONS

Forshew et al. Cancer Genomics 2012; 4: 136ra68 (Year: 2012).*
Zhou, M-Y and Gomez-Sanchez, C.E. Current Issues in Molecular Biology 2000; 2: 1-7 (Year: 2000).*
International Search Report for PCT/US14/70226, dated Apr. 7, 2015.
Seguin-Orlando et al., Ligation Bias in Illumina Next-Generation DNA Libraries: Implications for Sequencing Ancient Genomes. PLoS One Oct. 29, 2013;8(10):e78575.
Roboklon. MICELLULA DNA. Emulsion & Purification Kit. Kit for creation of emulsions and subsequent DNA purification. For emulsion PCR (ePCR) and for nucleic acid amplifications in emulsions. Cat. No. 3600. Version 1.1.0 (Oct. 2013).
Aquino et al., Linear amplification followed by single primer polymerase chain reaction to amplify unknown DNA fragments: complete nucleotide sequence of Oropouche virus M RNA segment. J Virol Methods. Jan. 2004;115(1):51-7.
Shyamala et al., Single Specific Primer-Polymerase Chain Reaction (SSP-PCR) and Genome Walking. Methods Mol Biol. 1993;15:339-348.

* cited by examiner

SEQUENCE LISTING

```
<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<223> OTHER INFORMATION: P oligo

<400> SEQUENCE: 1
gtcggagtct gcgc                                                     14
```

```
<210> SEQ ID NO 2
<211> LENGTH: 11
<212> TYPE: DNA
<213> ORGANISM: Artificial Sequence
<220> FEATURE:
<223> OTHER INFORMATION: T oligo

<400> SEQUENCE: 2
agactccgac t                                                              11
```

METHODS FOR FULL-LENGTH AMPLIFICATION OF DOUBLE-STRANDED LINEAR NUCLEIC ACIDS OF UNKNOWN SEQUENCES

REFERENCE TO RELATED APPLICATION

This application is a national stage application (under 35 U.S.C. 371) of PCT/US2014/070226 filed on 14 Dec. 2014, which claims priority to U.S. provisional application 61/916,271 filed on 15 Dec. 2013, all of which are herein incorporated by reference in their entireties.

FIELD OF THE INVENTION

The present invention relates generally to DNA amplification.

BACKGROUND OF THE INVENTION

The advances in sequencing technology have provided a superior alternative for the detection of cancer mutations. Next-generation sequencing (NGS) is a cutting age technology with a superior resolution capable of reaching down to the single nucleotide level. However, the application of NGS in the analysis of cancer mutations from circulating plasma DNA (ctDNA), which may carry a small amount of tumor circulating DNA (ctDNA A), is still at an early stage. This is due to the fact that the DNA level in plasma is extremely low and that there are not many reliable methods to amplify a small amount of DNA from the plasma. Conventional DNA amplification by polymerase chain reaction (PCR) utilizes one or more primer "pairs" to define the boundaries of a target region(s) and prime the synthesis by thermophilic DNA polymerase.

The strategy of using paired primers has an intrinsic disadvantage when being applied to full-length amplification of linear DNA because it is essential for the termini of each target DNA fragment to ligate to two different adapters, which will enable the binding of different PCR primers for cyclic DNA amplification. Since every terminus has equal chance to bind to either adapter, half of the DNA fragments are ligated to only one type of adapter, resulting in a 50% potential loss of sequence information because of the inability of such fragments to be amplified at exponential rate and thus will become mistakenly underrepresented in sequencing and downstream analysis. This problem can be troublesome when it comes to NGS analysis of low abundance DNA molecules such as those in single-cell transcriptome or those in body fluid specimens such as plasma, where the majority of target DNA or RNA species are far below the minimal level required for sequencing library construction or for quantification by conventional laboratory instruments. This problem can become even more severe when disease diagnosis is concerned, because a huge number of clinical DNA samples are examined on daily basis and significant portion of these samples are of low quantity or low quality due to various reasons such as paraffin-embedding, long or improper storage, or at a small volume or a low concentration. Therefore, an efficient and nonselective DNA amplification method which is able to target and amplify "all" DNA/RNA molecules, without sequence discrimination, in the sample is strongly desired.

SUMMARY OF THE INVENTION

The invention relates to development of a novel approach, called TOP-PCR (T-oligo primed PCR).

In one aspect, the invention relates to a method of amplifying a linear, double-stranded nucleic acid of unknown sequence. The method comprises the steps of:
(a) providing the linear, double-stranded nucleic acid of unknown sequence;
(b) adding one adenine nucleotide (A) to the 3'-tails of the linear, double-stranded nucleic acid of unknown sequence to obtain a target nucleic acid of unknown sequence with 3'-adenine nucleotide (3'-A) overhangs;
(c) providing a first strand oligonucleotide (oligo) with a 5'-phosphate (5'-p);
(d) providing a second strand oligonucleotide (oligo) with a 3'-thymine nucleotide (3'-T) and without a 5'-phosphate (5'-p) the second strand oligo with a 3'-T being complimentary to the first stand oligo with a 5'-p except at the 3'-T of the second strand oligo;
(e) annealing the first and the second strand oligos to generate a homogeneous adapter with one 3'-T-overhang;
(f) ligating the homogeneous adapter to the target nucleic acid of unknown sequence with 3'-A overhangs to form an adapter-ligated target nucleic acid of unknown sequence with the adapter attached at each end thereof; and
(g) performing a polymerase chain reaction (PCR) with the adapter-ligated target nucleic acid of unknown sequence as a template and the second strand oligo with a 3'-T as a single primer to obtain a PCR product, wherein the full length of the nucleic acid of unknown sequence is amplified.

In one embodiment of the invention, the method comprises only one ligation step.

In another embodiment of the invention, the adapter does not self-ligate.

In another embodiment of the invention, the linear, double-stranded nucleic acid of unknown sequence is a body fluid DNA.

In another embodiment of the invention, the linear, double-stranded nucleic acid of unknown sequence is a circulating DNA obtained from the plasma of a cancer patient.

In another embodiment of the invention, the adapter has one 3'-T overhang and one 3'-non-A overhang.

In another embodiment of the invention, the adapter has one 3-overhang and one blunt end.

In another aspect, the invention relates to a method for assessment of a cancer-specific mutation and/or for cancer diagnosis. The method comprises the steps of:
(i) amplifying the full length of a linear, double-stranded nucleic acid of unknown sequence according to claim 1 to obtain a PCR product, wherein the linear, double-stranded nucleic acid is a body fluid-circulating DNA (ctDNA) from a patient;
(ii) sequencing the PCR product to obtain the sequence of the body fluid-ctDNA,
(iii) mapping the sequence of the body fluid-ctDNA against a public known genome sequence database to identify the presence or absence of a sequence variation;
(iv) making a cross-library comparison between the body fluid-ctDNA and DNA from buffy coat or white blood cells if the presence of a sequence variation is identified; and
(v) assessing the presence or absence of a cancer-specific mutation or a normal variation based on the results of the cross-library comparison.

In one embodiment of the invention, the aforementioned, method requires the following elements:
(1) the sequencing step is performed in parallel with a genomic DNA from buffy coat or white blood cells from the same subject;
(2) the mapping step is performed by mapping the sequence of the body fluid-ctDNA and the sequence of the genomic DNA of buffy coat or white blood cells against the public known genome sequence database;
(3) the cross-library comparison identifies variations in the body fluid-ctDNA and in the buffy coat or white blood cell DNA, and
(4) the assessing step further comprises subtracting the variations in the buffy coat or white blood cell DNA from the variations found in the body fluid-ctDNA to identify potential cancer mutations.

In another embodiment of the invention, the variation is selected from the group consisting of SNPs, insertions, and deletions.

In another embodiment of the invention, prior to step (b) the method further comprises performing an end-repair reaction to the linear, double-stranded nucleic acid or the body fluid-ctDNA of unknown sequence.

In another embodiment of the invention, the body fluid is selected from the group consisting of blood, saliva, semen, vaginal fluid, and amniotic fluid.

In another embodiment of the invention, the amount of the linear, double-stranded nucleic acid of unknown sequence is no greater than 20 copies.

In another embodiment of the invention, the amount of the linear, double-stranded nucleic acid of unknown sequence is no greater than 10 copies.

In another embodiment of the invention, the amount of the linear, double-stranded nucleic acid of unknown sequence is no greater than 5 picograms.

In another embodiment of the invention, the amount of the linear, double-stranded nucleic acid of unknown sequence is no greater than 0.01 picograms.

In another embodiment of the invention, the adapter-ligated target nucleic acid of unknown sequence does not circularize or form a circular nucleic acid.

In another embodiment of the invention, the PCR is performed in the absence of heterogenous primers.

In another embodiment of the invention, the ligating step is preformed in the absence of heterogenous adapters.

The length of the nucleic acid of unknown sequence may be about 100 bp-2 kb. The PCR efficiency may decrease if the length of the nucleic acid template is larger than 2 kb.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 2 shows plasma DNA after 20-cycle TOP-PCR amplification. A total of 8 μl plasma DNA was taken from a 16 μl stock and used for end repair, A-tailing, and ligation to a homogenous adapter, followed by purification with AMPURE® XP beads. Purified DNA sample was amplified by PCR for 20 cycles and purified again with AMPURE®. The elute was kept in 5 μl of nuclease-free water, of which 1 μl was used for BIOANALYZER® analyses. The total amount of DNA (with a peak at 424 bp) was quantitated by BIOANALYZER® to be 102 pg/μl. Based on the data, the plasma DNA concentration in the original 16 μl of stock was ~0.1 fg/μl (see FIG. 1).

FIG. 3 shows plasma DNA after 30-cycle TOP-PCR amplification. A total of 8 μl of an original plasma DNA was end-repaired, A-tailed, ligated to a homogenous adapter, and then amplified for 30 cycles with T oligo of the adapter. One μl of the post-amplified plasma DNA was measured by BIOANALYZER®. The size of DNA molecules ranges from ~100 bp to over 2,000 bp.

FIG. 7 is a schematic drawing showing plasma DNA amplification by TOP-PCR. Complimentary oligos (labeled as T-oligo and P-oligo) are synthesized by oligo synthesizer. Only the P-oligo has a phosphate group in the 5'-end. Annealing at room temperature allows these two oligos to form a homogeneous sticky adapter, which can ligate only to the ends (termini) of plasma DNA molecules. Since there is no 5'-phosphate roup in the T-oligo, self-ligation of the sticky adapter is prevented. PCR amplification using T-oligo as the only PCR primer is able to efficiently amplify target plasma DNA molecules for sequencing and subsequently analysis. The P-oligo and T-oligo sequences are 5'-GTCG-GAGTCTgcgc-3' (SEQ ID NO: 1) and 5'-AGACTC-CGACT-3' (SEQ ID NO: 2), respectively.

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a". "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term. The scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein. "around". "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "coverage" in sequencing means "how many times a specific location is sequenced". For example, if there are a total of 30 sequence reads (produced by a sequencer) mapped to a particular genomic location, then the (sequencing) coverage of this location is 30-fold. For another example. If in position 1,000,000 of chromosome 10 is 'A', and in a library we have 25 sequence reads mapped to this site (i.e., 25 reads cover this position), then this position has 25-fold coverage. The unit, should be "times or folds of coverage". However, "coverage" per se is already a comprehensive term in genomics.

The terms "a discontinuous pattern" and "segmented patterns" are interchangeable.

The terms "cancer mutations" and "cancer genetic mutations" are interchangeable. Initially, cancer mutations refer to the genetic mutations found in cancer cells or cancer tissues, such as single base deviations, insertions, deletions, inversions, etc. With the increasing knowledge resulted from intensive cancer studies, it become clear that cancer is a very complicate disease resulted from multiple types of disorders at multiple levels, including alterations in genetic and epigenetic modifications, mitochondrial and nuclear DNA aberrations, chromosomal instability, and metabolic disorders.

An "adapter" consists of two strands of annealed oligonucleotides. The length of the oligio may be 10-20, preferably 20, nucleotides. Lower than 10 nucleotides in length may decrease specificity for annealing. Higher than 20 nucleotides in length may not be cost-effective. In one embodiment of the invention, the T oligo has 11 bp in length, e.g., sequence: 5'-AGACTCCGACT-3' (SEQ ID NO: 2). The illustrated P oligo sequence is 5'-GTCGGAGTCTgcgc-3' (SEQ ID NO: 1). Example of adapters are disclosed in U.S. Patent Publication No. 20120231508, which is incorporated herein by reference in its entirety.

The term "a homogeneous adapter" mean one single type of adapter.

The term "heterogeneous adapters" means at least two types of adapters that have different nucleotide sequences from each other.

"single" primer means only one type of primer is present, instead of a pair of primers. The term "heterogenous primers" means at least 2 different types of primers.

An "overhang" is a stretch of unpaired nucleotides at the end of a DNA molecule. These unpaired nucleotides can be in either 3' or 5' end, creating either 3' or 5' overhangs, respectively. When an overhanging end is palindromic, which means the nucleotide sequence of the overhang is a palindrome.

The term "3'-non-A overhang" means the 3'-end having a non-adenine overhang, i.e., a 3'-overhang that does not have an extra adenine nucleotide.

The term "body fluid-ctDNA" refers to circulating DNA obtained from a body fluid.

We have developed a robust DNA amplification strategy called "T oligo-primed polymerase chain reaction (TOP-PCR)", designed for efficient, nonselective, full-length amplification of trace amount of linear DNA. Concordant with modern molecular cloning and NGS sequencing strategies, which frequently add an extra 'A' to both 3' ends of a target DNA, we adopted a homogeneous double-stranded adapter strategy which carries one extra 'T' at the 3' end (i.e., 3'-T overhang) for sticky-end ligation to all target DNA fragments. We were able to amplify, in full-length, the DNA fragments from low abundance or partially degraded plasma DNA samples. By doing so, the resolution of sequence analysis was dramatically increased and old samples were rescued.

According to the method of the invention, the sequence information of the nucleic acids is unknown or unavailable. Both unknown ends of the nucleic acids are caused tollgate to a suitable homogenous adapter. The adapter consists of 2 oligos of known sequences (P-oligo and T-oligo), in which T-oligo serves as the only one PCR primer. The nucleic acids are then amplified with the T-oligo annealing to the P-oligo of the homogeneous-adapter. All the nucleic acids of unknown sequences in the sample can be amplified completely.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

The invention relates to a novel detection method which is able to discover any tumor mutations, either intragenic or intergenic, that may be present in plasma. Circulating plasma DNA would act as a channel allowing us to access and analyze any cancer mutations as long as the mutations are flowing through the channel. Plasma DNA amplification represents a great challenge and requires a robust molecular amplification strategy. We have successfully tested the strategy of using TOP-PCR to amply ctDNA from the plasma obtained from a metastatic ovarian cancer patient. The amplified ctDNA sample was sequenced in parallel with tumor (genomic) DNA for cross-tissue comparison. We identified significant numbers of concurrent point mutations (i.e. mutations found in both plasma DNA and tumor DNA), representing a detectable data-wise overlap in mutated locations between ctDNA and tumor DNA. Taken together, results from these proof-of-concept experiments demonstrate the feasibility of using a homogenous adapter and T oligo as a single primer in TOP-PCR for plasma DNA-mediated detection of tumor mutations and for cancer diagnosis. This method is rapid and robust.

Evaluation of an Original, Pre-Amplified Plasma DNA Sample From a Metastatic Ovarian Cancer Patient Using BIOANALYZER®

Although the quantity of plasma DNA was not expected to be observable under BIOANALYZER™, all plasma DNA samples need to be quantified by BIOANALYZER®, or equivalent devices, for initial recording. One may want to choose qPCR instead of BIOANALYZER® for the initial quantification, but the latter is recommended because it is easier to run BIOANALYZER® than qPCR, and the effect of amplification with a homogenous-adapter according to the invention can be readily distinguished by comparing the pre- and post-amplified samples using BIOANALYZER®.

Experimental Procedure.

Figure 1:
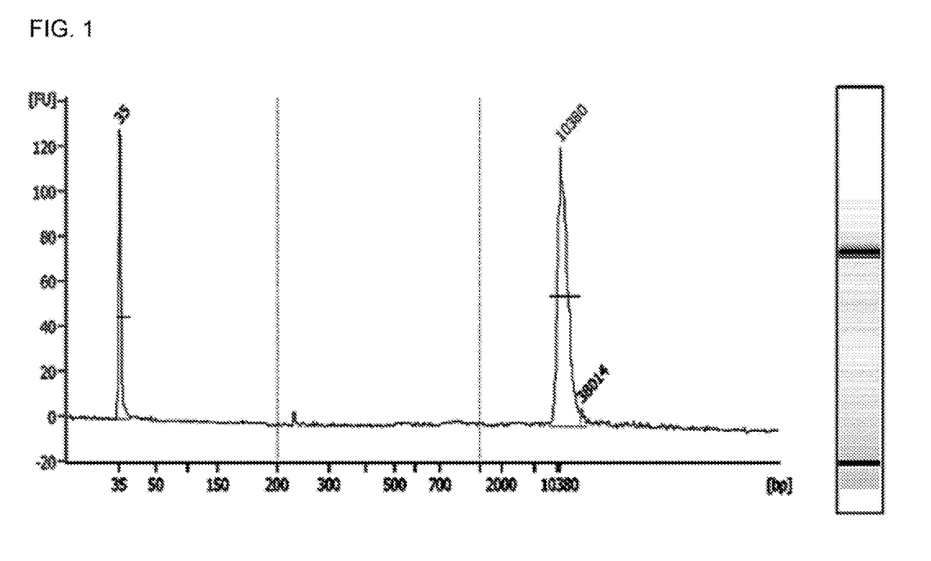
FIG. 1 shows an original plasma DNA sample from a metastatic ovarian cancer patient measured by BIOANALYZER®. One micro-liter of an original (most concentrated) plasma DNA sample was used in this quantification by BIOANALYZER®. Peaks at 35 bp and 10,380 bp are size markers. All DNA molecules, if present in the plasma sample, are expected to be present between these two markers based on known DNA size distribution in the plasma. FU stands for "Fluorescence Unit". Bioanalyzer uses fluorescent labeling to detect DNA concentration. Based on the quantity of T-oligo primed PCR (TOP-PCR) amplified plasma DNA (as estimated by BIOANALYZER®, see FIG. 2), the total amount of plasma DNA displayed in this figure was estimated to be ~0.1 femto-gram (fg) per micro-liter.
Figure 2:
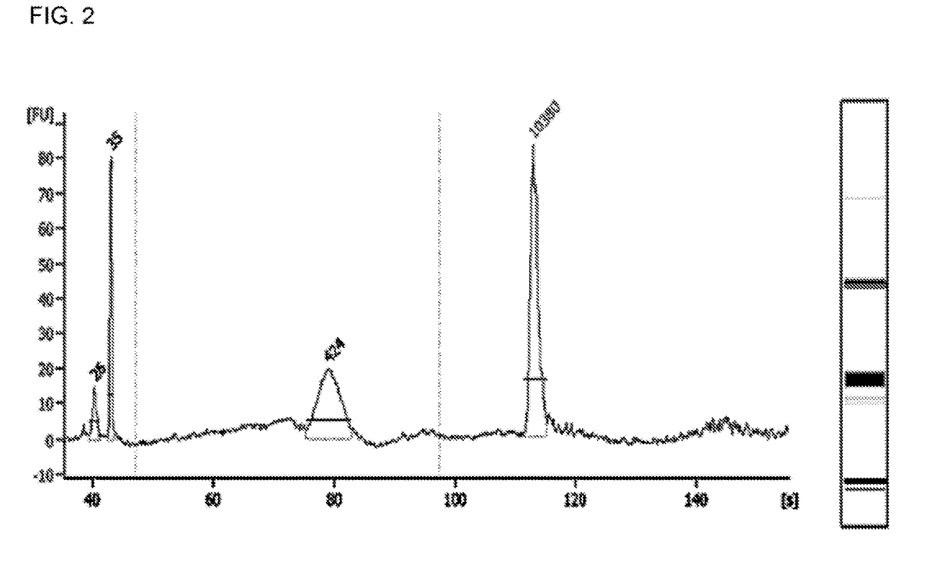
Figure 3:
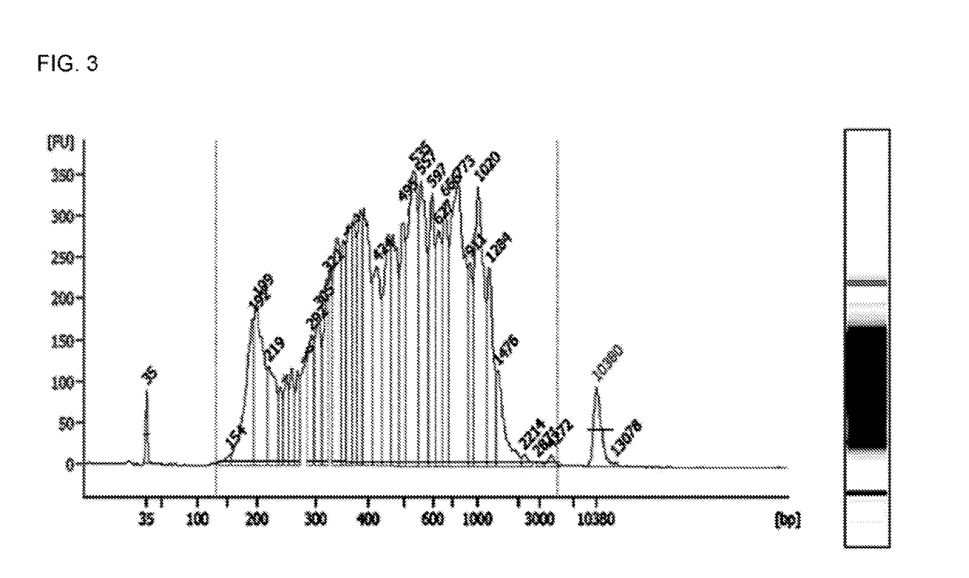

One µl of original plasma DNA (prepared in ddH₂O) from an ovarian cancer patient was quality evaluated and quantity estimated by BIOANALYZER® (Agilent 2100). The pre-amplification plasma DNA sample, as measured by BIO-ANALYZER®, is shown in FIG. 1. The quantity of plasma DNA in this sample was found way below the minimal detectable level of BIOANALYZER®.

End-repair and A-tailing

Plasma DNA molecules were end-repaired, tailed an 'A' to every 3' end, and ligated to a homogenous adapter according to the invention.

Amplification of Plasma DNA With a Homogenous Adapter and T Oligo

Figure 7:
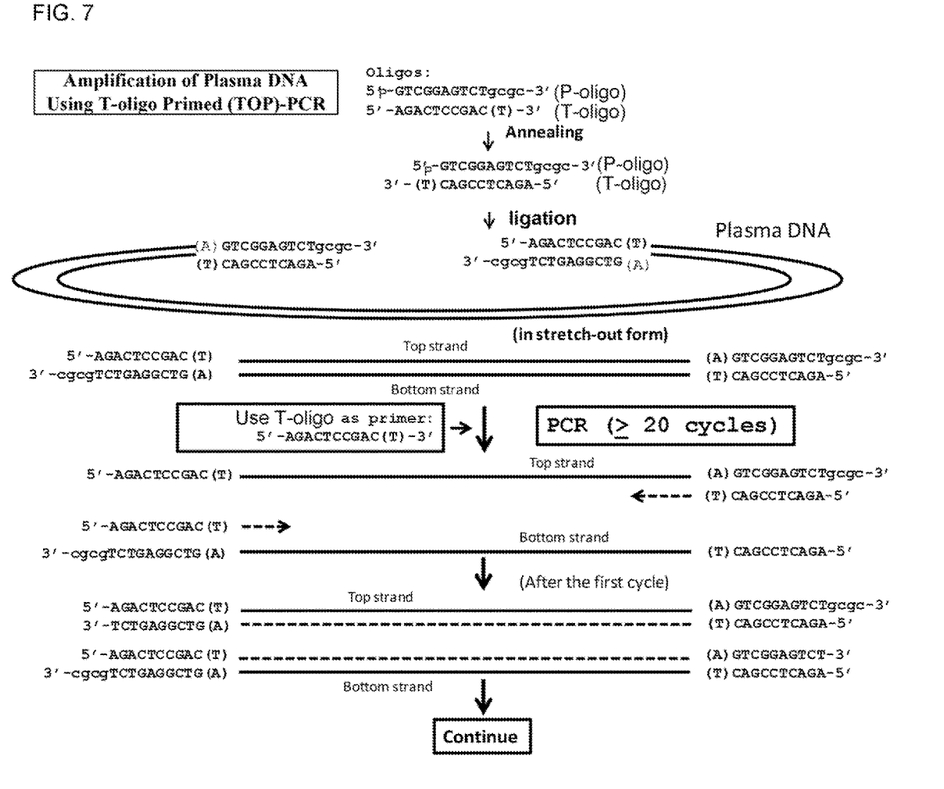

PCR amplification was conducted by using the T oligo of the adapter. In one embodiment of the invention, the T-oligo sequence is 5'-AGACTCCGACT-3' (SEQ ID No: 2), as shown in FIG. 7.

DNA Purification

The TOP-PCR-amplified plasma DNA samples can be purified by AMPURE® XP kit, or gel excision.

DNA Sonication

Figure 4:
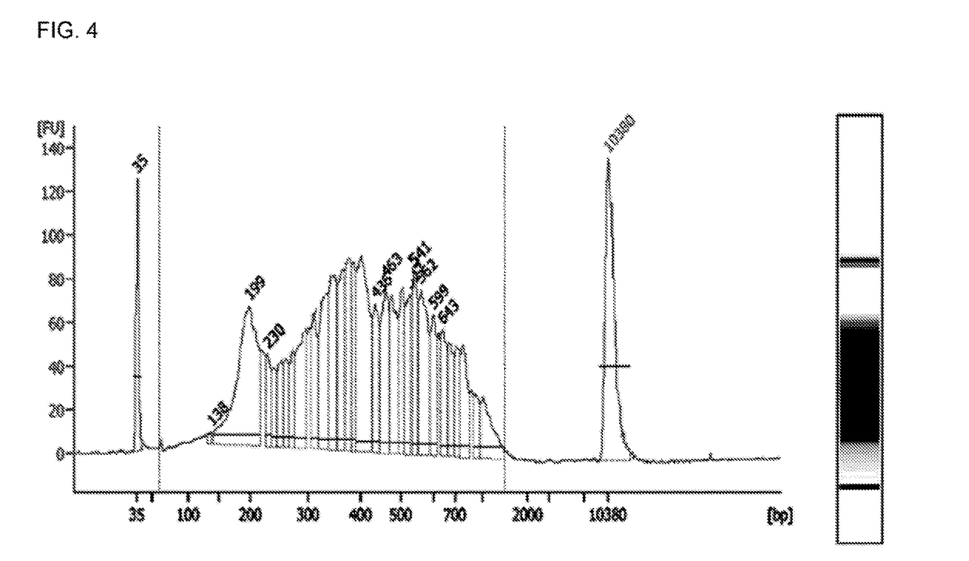
FIG. 4 shows plasma DNA after 30-cycle TOP-PCR amplification and sonication. Sonication was conducted with COVARIS™ sonicator. The size of DNA fragments now ranges between ~100 to 1,000 bp.

Corvaris sonicator was used. Sonicated, amplified plasma DNA samples were evaluated by BIOANALYZER® (FIG. 4), end-repaired, A-tailed, and then ligated to sequencing adapter for making sequencing libraries.

During sequencing library construction, the sequencing adapter-ligated DNA samples were purified with AMPURE® XP beads, amplified by conventional PCR method to expand the adapter-ligated DNA, and then purified with AMPURE® beads to select 300 bp-500 bp DNA fragments.

Sequencing libraries were quantified with qPCR and loaded into MISEQ™ sequencer for cluster generation. The prepared libraries were sequenced with 250×250 (bp) PE sequencing. The generated sequence reads were then analyzed.

Overall Workflow

Figure 5:
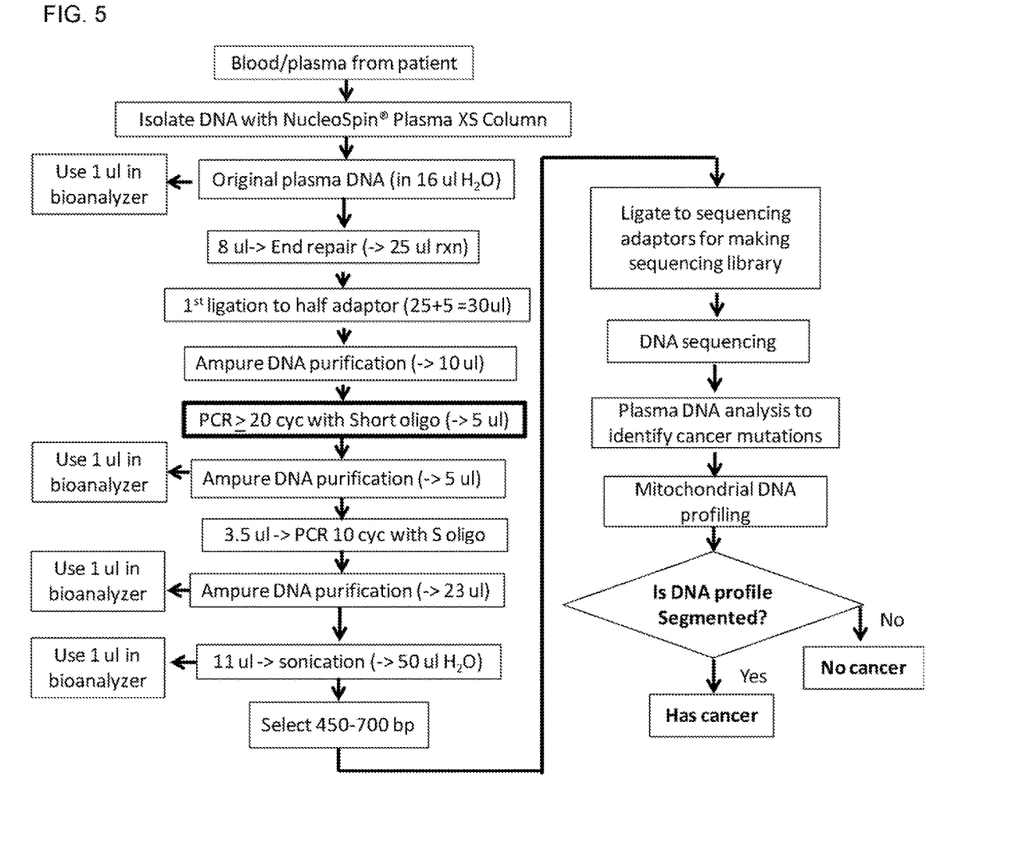
FIG. 5 shows overall workflow for plasma DNA analysis.

The workflow for analyses is outlined and shown in FIG. 5.

Figure 6:
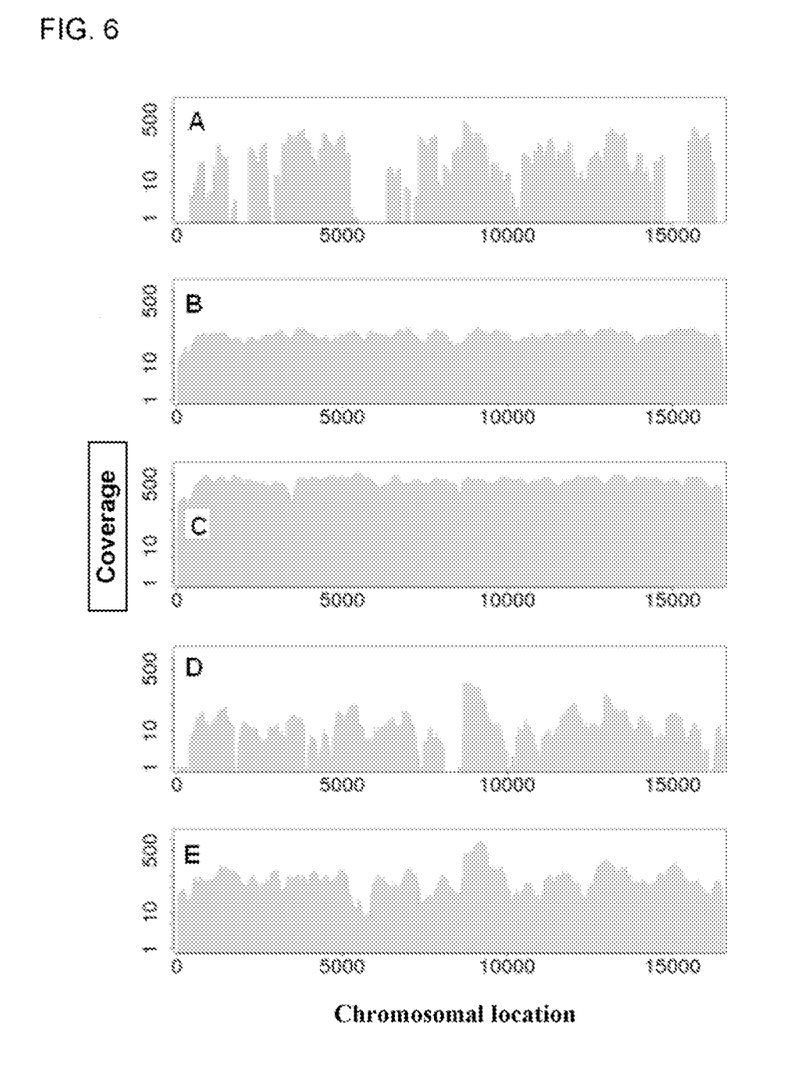
FIG. 6 shows mitochondrial DNA profiles of TOP-PCR-rescued plasma ctDNA samples, genomic DNA samples from cancer patients, and normal fresh plasma ctDNA control. Plasma DNA samples from various sources were amplified by a homogenous adaptor system and sequenced by MISEQ™ sequencer. The generated sequence reads were mapped against human mitochondrial genome included in hg19 (UCSC database) and then displayed. A) mtDNA profile from TOP-PCR-amplified (degraded) plasma DNA of an ovarian cancer patient. B) mtDNA profile from buffy coat DNA of the same ovarian cancer patient. C) mtDNA profile from tumor tissue of the same ovarian cancer patient. D) mtDNA profile from TOP-PCR-amplified (degraded) plasma. DNA of an Early Onset Breast Cancer patient. E) mtDNA profile from TOP-PCR-amplified (fresh) plasma DNA of a normal female control.

Cancer Patient-specific Mitochondrial DNA Profile Discontinuities Revealed by TOP-PCR Amplification Strategy Here we use mtDNA profiling as an example to demonstrate the robustness of a homogenous-adapter amplification strategy. As shown in FIG. 6, the presence of gaps (discontinuities) in mtDNA profile were found only in old plasma DNA samples.

Adapter Design for Use in T-oligo Primed-PCR Amplification

Figure 8:
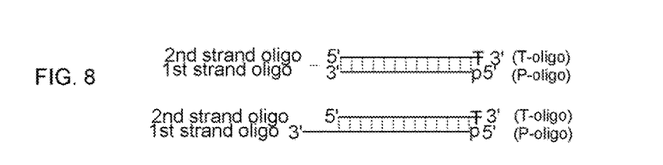
FIG. 8 is a schematic drawing illustrating the design of adapters.

The adapter consists of double strands of oligonucleotides. One strand is called T-oligo, which has an extra thymine nucleotide (T) at the 3'-end. The other strand is called P-oligo, which has a phosphate group at the 5'-end, and its 3'-end nucleotide has no extra T. The adapter may be a blunt-sticky (i.e., one end is blunt and the other end is sticky) or double sticky (i.e., both ends are sticky) adapter. See FIG. 8, top and bottom panel, respectively. For the "blunt-sticky" adapter, the P-oligo is 1 base shorter and is complementary to the T-oligo except at the 3'-end T of the T-oligo. For the "double-sticky" adapter, the P-oligo is longer than the T-oligo (FIG. 8). There are five requirements for the "adapter": 1) One strand (called T-oligo) needs to have an extra 3'-T (i.e., 'T' overhang at the 3' end); 2) T-oligo has no 5'-phosphate; 3) The other strand (P-oligo) requires a 5'-phosphate; 4) With the exception of its 3'-end T, the length of the T-strand is shorter than or equal to the length of the P-strand; and; 5) Only the T-oligo is used as the PCR primer for the TOP-PCR amplification.

Assessment of Cancer Genetic Mutations

Both buffy coat DNA (used as normal control) and plasma DNA need to be collected from the same cancer patient or person to be tested. The plasma DNA can be either amplified or not amplified by TOP-PCR depending on its initial concentration and then sequenced, while the buffy coat DNA does not require TOP-PCR amplification and is directly sequenced. Then, both the plasma DNA sequences and the buffy coat sequences are mapped against the reference genome (e.g. hg19 of UCSC database) to identify the variations (especially SNPs, insertions and deletions) in plasma DNA and buffy coal DNA. Variations in buffy coat DNA is subtracted from the variations found in plasma DNA. Some variations (e.g. SNPs found in normal healthy individuals) are considered as "normal variations" and, as such, should be ignored. The rest of variations in plasma DNA are likely to be derived from cancer cells (i.e., potential cancer genetic mutations).

Cross-library Comparison

Case #1

Normal genome sequence database: nnnnnnnnnnnnnnnTnnnnnnnn
(1) cancer tissue: nnnnnnnnnnnnnnnAnnnnnnnn
(2) plasma DNA: nnnnnnnnnnnnnnnAnnnnnnnn
(3) WBC DNA: nnnnnnnnnnnnnnnTnnnnnnnn The results of cross-library comparison indicate, a cancer mutation.

Case #2 (not a mutation)

Normal genome sequence database: nnnnnnnnnnnnnnnGnnnnnnnn
(1) cancer tissue: nnnnnnnnnnnnnnnTnnnnnnnn
(2) plasma DNA: nnnnnnnnnnnnnnnTnnnnnnnn
(3) WBC DNA: nnnnnnnnnnnnnnnTnnnnnnnn The results of cross-library comparison indicate not a mutation.

Unique Features of the Invention/Advantages When Compared to Existing Technologies Procedures adopted previously by other groups (e.g. by Dawson et al. and Forshew et al.) were tedious and relied heavily on commercial instruments, resulting in very limited scope of gene mutation screening capability. Their approaches can only analyze very limited numbers of known cancer genes and thus are not suitable for global detection of both known and unknown novel cancer mutations. The method of the invention has no limitation in the number of genes or genetic locations (both intragenic and intergenic locations can be detected) that can be screened for cancer mutations or used for cancer diagnosis via plasma DNA analyses.

The unique features of the present invention are as follows:
(1) Unlike conventional PCR primers, T oligo is the ONLY ONE primer used in PCR.
(2) PCR amplification with TOP-PCR is highly efficient;
(3) The procedure of the invention is extremely simple and straightforward;
(4) The method of invention detects all types of mutations, including intragenic and intergenic cancer mutations, either known or novel, while previous methods were limited to a few known genes; and
(5) The method of the invention works in harmony with NGS sequencers, which are currently the most sensitive instruments for DNA sequencing and also use A-tailing in target DNA for ligation with sequencing adapters, while the other methods require more instruments such as digital PCR or rtPCR machine.

Utility of the Invention

During the evolution of biotechnologies, the most powerful and simplest approach has higher chance to survive evolutionary selection. According to the invention, the method has ample advantages over the other methods and thus has a greater chance to be selected for being used on clinical samples for early cancer detection, or even for regular usage in the lab. Kits may be generated for use in the detection method according, to the invention.

TOP-PCR can amplify RNA if the RNA molecules are converted to cDNA.

Some plasma samples already have enough DNA, thus there is no need to amplify these samples by TOP-PCR. TOP-PCR is especially useful for low abundance plasma DNA samples such as those with prolonged storage (e.g., over 3 or 4 years) or those with repetitive freeze-and-thaw cycles.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which ma include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of amplifying a linear, double-stranded nucleic acid of unknown sequence, comprising the steps, of:
   (a) providing the linear, double-stranded nucleic acid of unknown sequence;
   (b) adding one adenine nucleotide (A) to the 3'-tails of the linear, double-stranded nucleic acid of unknown sequence to obtain a target nucleic acid of unknown sequence with 3'-adenine nucleotide (3'-A) overhangs;
   (c) providing a first strand oligonucleotide (oligo) with a 5'-phosphate (5'-p);
   (d) providing a second strand oligonucleotide (oligo) with a 3'-thymine nucleotide (3'-T) and without a 5'-phosphate (5'-p), the second strand oligo with a 3'-T being complementary to the first strand oligo with a (5'-p except at the 3'-T of the second strand oligo;
   (e) annealing the first and the second strand oligos to generate a homogeneous adapter with one 3'-T-overhang;
   (f) ligating the homogeneous adapter to the target nucleic acid of unknown sequence with 3'-A overhangs to form an adapter-ligated target nucleic acid of unknown sequence with the adapter attached at each end thereof; and
   (g) performing a polymerase chain reaction (PCR) with the adapter-ligated target nucleic acid of unknown sequence as a template and the second strand oligo with the 3'-T as a single primer to obtain a PCR product, and thereby the fall length of the nucleic acid of unknown sequence is amplified,
   wherein the homogeneous adapter has one 3'-T overhang and one 3'-non-A overhang.

2. The method of claim 1 which comprises only one ligation step.

3. The method of claim 1, wherein the adapter does not self-ligate.

4. The method of claim 1, wherein the linear, double-stranded nucleic acid of unknown sequence is a body fluid DNA.

5. The method of claim 4, wherein the body fluid is selected from the group consisting of blood, saliva, semen, vaginal fluid, and amniotic fluid.

6. The method of claim 1, wherein the linear, double-stranded nucleic acid of unknown sequence is a circulating DNA obtained from the plasma of a cancer patient.

7. The method of claim 1, wherein the amount of the linear, double-stranded nucleic acid of unknown sequence is no greater than 5 picograms.

8. The method of claim 7, wherein the amount of the linear, double-stranded nucleic acid of unknown sequence is no greater than 0.01 picograms.

9. The method of claim 1, wherein the adapter-ligated target nucleic acid of unknown sequence does not circularize or form a circular nucleic acid.

10. A method for assessment of a cancer-specific mutation and/or for cancer diagnosis, comprising the steps of:
   (i) performing the method of claim 1 to obtain the PCR product, wherein the linear, double-stranded nucleic acid of the unknown sequence in step (a) is a body fluid-circulating DNA (ctDNA) of unknown sequence from a patient;
   (ii) sequencing the PCR product to obtain die sequence of the body fluid-ctDNA;
   (iii) mapping the sequence of the body fluid-ctDNA against a public known genome sequence database to identify the presence or absence of a sequence variation;
   (iv) making a cross-library comparison between the body fluid-ctDNA and DNA from buffy coat or white blood cells if the presence of a sequence variation is identified; and
   (v) assessing the presence or absence of a cancer-specific mutation or a normal variation based on the results of the cross-library comparison.

11. The method of claim 10, wherein:
   (1) the sequencing step is performed in parallel with genomic DNA from huffy coat or white blood cells from the same patient;
   (2) the mapping step is performed by mapping the sequence of the body fluid-ctDNA and the sequence of the genomic DNA of buffy coat or white blood cells against the public known genome sequence database;
   (3) the cross-library comparison identifies variations in the body fluid-ctDNA and in the huffy coat or white blood cell DNA, and
   (4) the assessing step further comprises subtracting the variations in the huffy coat or white blood cell DNA from the variations found in the body fluid-ctDNA to identify potential cancer mutations.

12. The method of claim 10, wherein the variation is selected from the group consisting of SNPs, insertions, and deletions.

13. The method of claim 10, prior to step (b) further comprising performing an end-repair reaction on the body fluid-ctDNA of unknown sequence.

14. The method of claim 10, wherein the body fluid is selected from the group consisting of blood, saliva, semen, vaginal fluid, and amniotic fluid.

15. The method of claim 10, wherein the amount of the linear, double-stranded nucleic acid of unknown sequence is no greater than 20 copies.

16. The method of claim 15, wherein the amount of the linear, double-stranded nucleic acid of unknown sequence is no greater than 10 copies.

* * * * *